United States Patent [19]
Findl

[11] 3,951,521
[45] Apr. 20, 1976

[54] REVERSIBLE RADIANT ENERGY FILTER AND PROCESS OF USING SAME

[75] Inventor: Eugene Findl, Granada Hills, Calif.

[73] Assignee: Xerox Corporation, Stamford, Conn.

[22] Filed: June 6, 1969

[21] Appl. No.: 831,059

Related U.S. Application Data

[63] Continuation-in-part of Ser. No. 371,927, June 2, 1964, abandoned.

[52] U.S. Cl. ............................ 350/160 R; 350/312
[51] Int. Cl.² ........................................... G02F 1/17
[58] Field of Search ........... 350/160, 161, 147, 151, 350/312

[56] References Cited
UNITED STATES PATENTS

| | | | |
|---|---|---|---|
| 2,632,045 | 3/1953 | Sziklai | 350/160 |
| 3,169,163 | 2/1965 | Nassenstein | 350/160 |
| 3,283,656 | 11/1966 | Jones et al. | 350/160 |
| 3,303,488 | 2/1967 | Anderson | 350/160 |

*Primary Examiner*—William L. Sikes
*Attorney, Agent, or Firm*—A. A. Mahassel; J. E. Beck; Irving Keschner

[57] ABSTRACT

This application relates to an electrolytic process for regulating the transmission of radiant energy, and a radiant energy filter for use in said process. The filter comprises a first film having a dye and a first ionic species therein, an adjacent second film having a second ionic species therein, said first ionic species and said second ionic species being related by a reversible electrochemical reaction, and barrier means positioned between said first and second films for preventing the passage therethrough of said dye, said first ionic species, and said second ionic species but permitting the passage therethrough of current-carrying ions. By passing current through said filter, the color of said dye can be caused to change whereby the transmission of radiant energy can be regulated.

9 Claims, 3 Drawing Figures

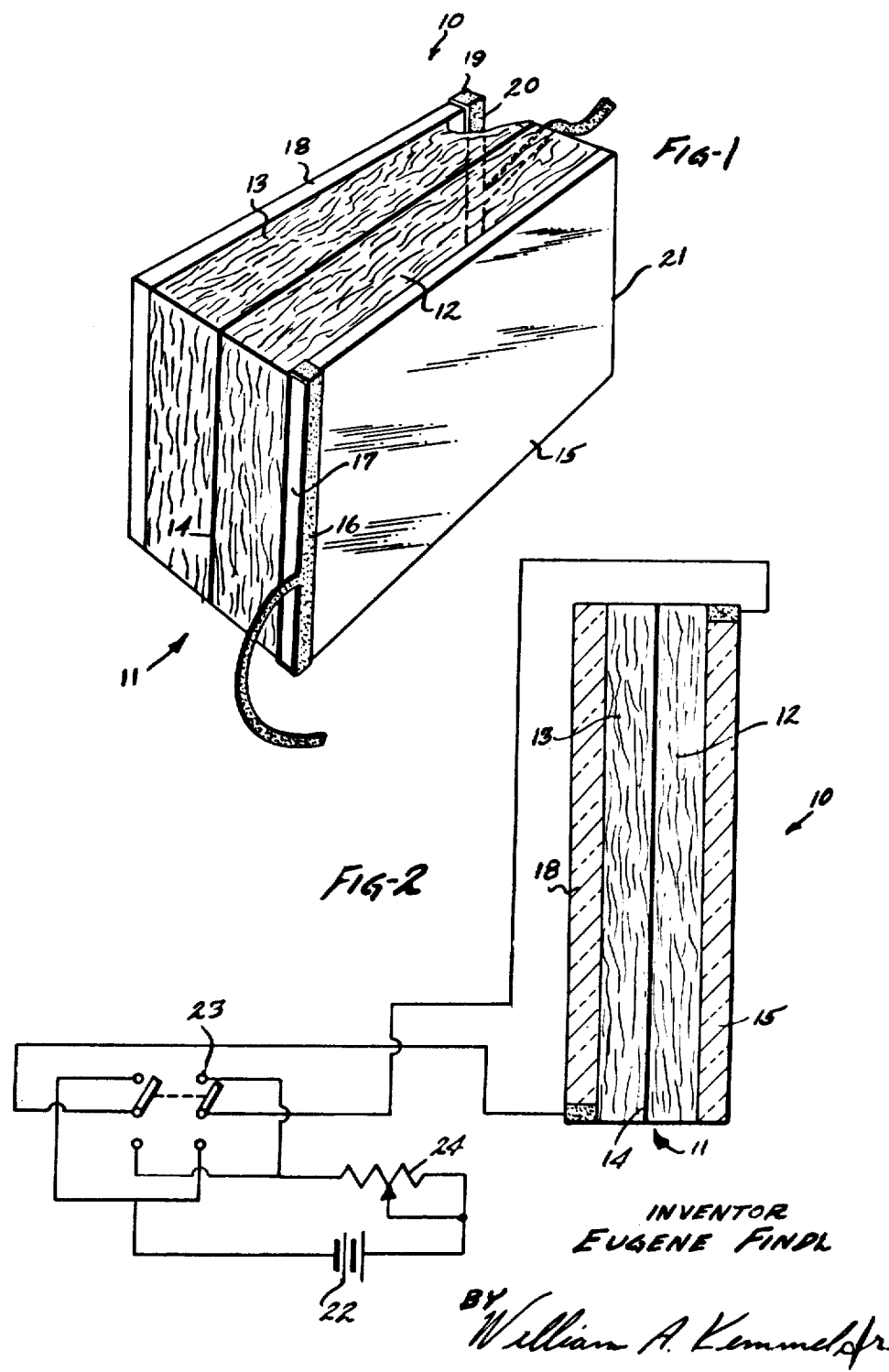

REVERSIBLE RADIANT ENERGY FILTER AND PROCESS OF USING SAME

CROSS REFERENCE TO PARENT APPLICATION

This application is a continuation-in-part application of application Ser. No. 371,927 filed June 2, 1964, and now abandoned both applications being assigned to the same assignee.

BACKGROUND OF THE INVENTION

This application relates to a method for reversibly filtering radiant energy and radiant energy absorption means therefor. More particularly, the present invention involves an efficient, easily reversible electrolytic process for regulating the transmission of radiant energy requiring a low electrical potential. The present invention also relates to a radiant energy filter adapted for use with the above-identified transmission regulation process. As used in the present application, the term "radiant energy" refers not only to the visible portion of the radiant energy spectrum but also to other forms of radiation, such as infra-red and ultra-violet.

To date, the methods and devices for regulating the transmission of radiant energy have involved, usually, mechanical or electro-mechanical devices. Typical examples of such devices are the shutters used on the normal building window or on a camera, as well as the filters which can be mounted over the window or over the camera lens. However, such prior art devices have a number of disadvantages. A basic disadvantage is that all such mechanical and electro-mechanical shutters and filters are external to the optical structure (i.e., the window or camera lens) and thus decrease the esthetic appeal of the optical part. Also, such structures are subject to mechanical positioning problems with respect to the optical part. Furthermore, shutters customarily restrict the field of vision of the optical system while the usual filter is not capable of adjustment with respect to the amount of radiant energy transmitted.

OBJECTS OF THE INVENTION

It is, therefore, an object of the present invention to provide a method for easily and reversibly regulating the transmission of radiant energy.

It is further object of the present invention to provide a novel radiant energy filter.

It is a further object of the present invention to provide a novel radiant energy filter based upon electrochemical principles wherein the color of a dye can be caused to change thereby regulating the transmission of radiant energy therethrough, said filter having, in various elements thereof, first and second ionic species which are related by a reversible reduction-oxidation electrochemical reaction.

It is a further object of the present invention to provide a process for the regulation of the transmission of radiant energy wherein once a particular color has been developed in the radiant energy filter, it may be permanently maintained by terminating the external potential.

Another object of the present invention is the provision of a method for the electrolytic regulation of the transmission of radiant energy which requires low electrical potential.

These and still further objects, features and advantages of the present invention will become apparent upon consideration of the following detail disclosure of specific exemplary embodiments thereof.

BRIEF SUMMARY OF THE INVENTION

The above and still further objects, features and advantages of the present invention are achieved, in accordance therewith, by providing a radiant energy filter comprising an electrolytically conductive layer comprising a first film having a first ionic species associated therewith, a second film having a second ionic species associated therewith, and a barrier means sandwiched therebetween. The first film also includes a dye dispersed therein, the color of which starts to change at a particular half-cell electrical potential. More particularly, the color of the dye starts to change at a particular electrical potential and continues a gradual color change over a known potential range. The first and second ionic species in the first and second films, respectively, are related by a reversible electrochemical reaction, that is, the species are related by a reversible reduction-oxidation equation whereby, by the application of external potential, the respective species can be made to change oxidation states. Also associated with the first film and the second film is at least a third ionic species suitable for conducting current through the electrolytically conductive layer. The afore-mentioned barrier means is adapted to prevent the passage therethrough of the dye, the first ionic species and the second ionic species but is adapted to permit the passage therethrough of at least the third ionic species, i.e., the current-carrying ions.

The dye is selected such that a reversible color reaction can be caused by the application of external potential to the radiant energy filter. This can be achieved, for example, by providing a dye which changes from a colorless to a colored state, or vice versa, or from a highly colored to a less colored state, or vice versa, at a particular electrical potential or potential range which will be traversed by the operation of the radiant energy filter during the course of external potential application thereto. A particularly suitable combination is where the dye begins to change color at a potential approximately mid-way between the respective half-cell potentials of the first and second ionic species, each half-cell potential being individually determined in the absence of the other ionic species and with reference to a standard hydrogen electrode.

On opposite sides of the electrolytically conductive layer are transparent, or at least translucent, electrodes through which transmission of the radiant energy being filtered is made. Since the electrodes will be in contact with the first and second films which will have various chemical species therein, the electrodes must be sufficiently chemically resistant so that they will not be adversely affected during prolonged use. A particularly suitable electrode is tin oxide coated glass which can be purchased under the trade name NESA glass, a product of Pittsburgh Plate and Glass Company, Pittsburgh, Pennsylvania.

In the transmission regulating process, a potential is applied to the radiant energy filter. By proper selection of the dye and the potential applied to the filter, the dye can be caused to change color at a particular half-cell potential whereby the transmission of radiant energy will be affected. By changing color, it is meant (a) going from a colorless state to a colored state, (b) going from a colored state to a colorless state, (c) going from a highly colored state to a less colored state or vice versa, or (d) going from one color to another color.

BRIEF DESCRIPTION OF THE DRAWINGS

To facilitate understanding of the present invention, reference will now be made to the appended drawings representing a preferred specific embodiment of the present invention. Such drawings should not be construed as a limitation upon the present invention which is properly set forth in the claims appended hereto.

In the drawings:

FIG. 1 is a broken away perspective view of a radiant energy filter produced in accordance with the present invention;

FIG. 2 is a schematic diagram of the filter device of FIG. 1 showing a suitable electric circuit for the operation thereof.

As illustrated in FIGS. 1 and 2, radiant energy filter 10 comprises an electrolytically conductive layer 11 having a first film 12, a second film 13, and barrier means 14 disposed therebetween. First film 12 has a dye dispersed therein which starts to change color at a particular half-cell potential. The first film 12 also includes a first ionic species capable of being oxidized or reduced to a different oxidation state from its initial oxidation state. Second film 13 has included therein a second ionic species which is also capable of being converted to a different oxidation state. As previously indicated, the first species and the second species are related by a reversible reduction-oxidation electrochemical reaction so that, upon application of external potential to the radiantenergy filter, the relative ratio of the ionic species in each film can be made to vary. With this ratio variation, a corresponding half-cell potential change will be occurring in each film. By the proper selection of the dye material, a particular electrical potential will be reached in the first film such that a color change will be effected. This color change will have associated therewith a corresponding change in the absorbance of the filter such that the optical density (in terms of input versus output) can be varied over reasonably wide ranges, or as desired.

Figure 3:
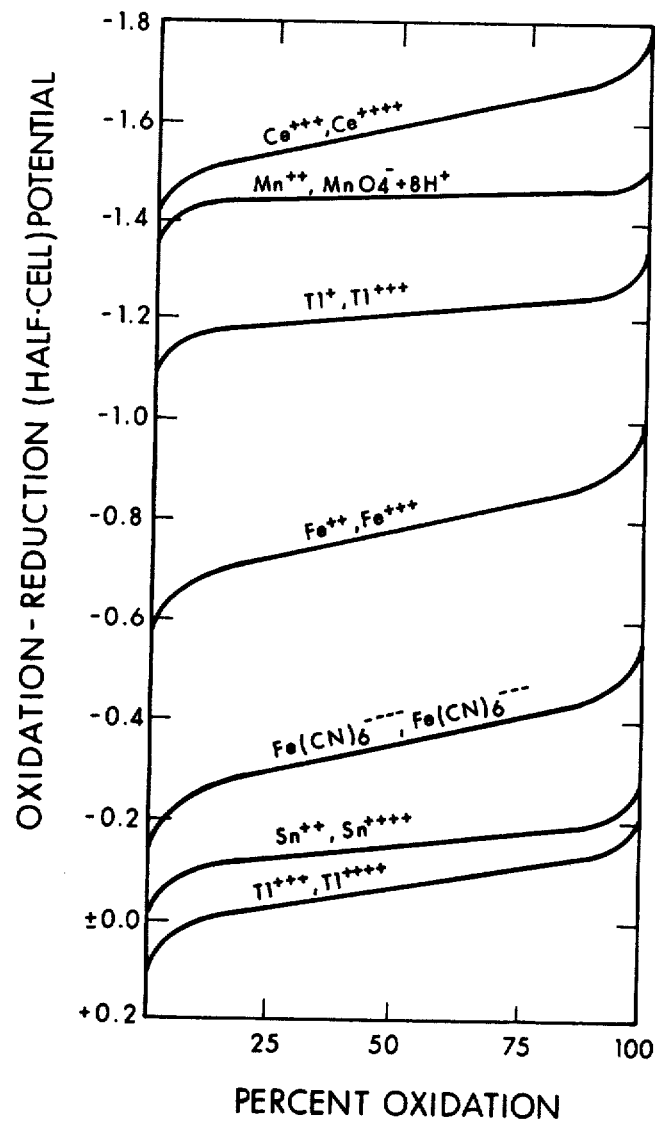
FIG. 3 is a chart illustrating the potential paths traversed by related ionic systems during the course of the application of external potential thereto.

Normally associated with the first ionic species and the second ionic species will be a third ionic species adapted for conducting current through the radiant energy filter. For example, when the first ionic species is the ferrous ion and the second ionic species is the ferric ion, the third ionic species can be chloride or sulfate ions which are common to both films 12 and 13. Sandwiched between first film 12 and second film 13 is barrier means 14 adapted to prevent the passage therethrough of the dye, the first ionic species and the second ionic species, but adapted to permit the passage therethrough of current-carrying ions, i.e., the third ionic species.

So that application of external potential can be made thereto, filter 10 includes transparent, or at least translucent, electrodes 15 and 18 disposed on opposite sides of films 12 and 13 and in contact therewith. Since the electrodes each have a finite resistivity, unless care is taken to equalize resistive paths, significant voltage gradiants will appear across the electrode surface. This can be eliminated by proper connection of the lead wires as shown in FIG. 1 where electrode 15 has an electrical connection 16 in the form of a bus bar extending over the entire length of one side thereof. The second electrode has electrical connection 19, also in the form of a bus bar, which also extends over the entire length of one side 20 thereof. Side 20 and side 21 are on diagonally opposite corners of electrodes 15 and 18. As illustrated in FIG. 2 the electrical circuit is completed by providing a battery 22, a double pole, double throw switch 23 and a variable resistance 24 between electrode 15 and electrode 18. Thus, the magnitude and direction of the electrical potential applied to the radiant energy filter 10 may be varied as desired. With the electrical connection as shown in FIG. 1, the resistive path from any point on the surface of one electrode to the bus bar on the opposite electrode is identical. Therefore, no significant variation in voltage across the electrode surface will appear.

From the nature of the barrier means, a physical separation of the ionic species and the dye results. That is, the first ionic species, including the dye material, and the second ionic species, or mixture thereof generated through the application of external potential thereto, remain separated on each side of the barrier means such that a static solution potential difference can exist across the barrier means which, once established, will be maintained. It follows that a particular color state once established will also be maintained in the absence of further externally applied potential serving to change electrical potential of the dye-containing film. Thus, once a particular color state, i.e., a particular filtering state, has been established, the external potential may be terminated or removed without adverse degradation of the filtering characteristics of the device. Since the barrier means maintains the static solution potential difference between the first film and the second film, the color state will be maintained, in the absence of an external potential serving to change the electrical potential of the first film. This is a fundamental characteristic of the filtering device of the present invention and enables continuing filtering operation even after the external potential has been terminated.

Since the device functions in a radiant energy transmission mode, the barrier means must also be transparent, or at least translucent. Suitable barriers include cellophane and slightly porous polyethylene containing ion-exchange resins. When using either of the aforementioned barrier means, films 12 and 13 may be in the form of aqueous solutions separated by the barrier means. Alternatively, the first and second films may be formed as solid sheets of a gel, such as hydroxy ethyl cellulose, with the actual barrier means being formed by the interface between the gel sheets. As previously indicated, the electrodes may be formed out of glass or transparent plastic, coated with a sufficiently inert conducting material, such as tin oxide.

The first ionic species of the present invention includes one or more ion members of the oxidized or reduced portion of a reversible electrochemical reduction-oxidation system. Similarly, the second ionic species of the present invention includes one or more ion members of the other portion of the same reversible electrochemical reduction-oxidation system. Thus, if the first ionic species corresponds to the reduced portion of the system, then the second ionic species corresponds to the oxidized portion of the same system. In this reduction-oxidation system, the relative ratios of each ionic species in each film can be varied by the application of an external potential to the filtering device. This change in the ratio of ionic species will be accompanied by a corresponding change in the half-cell potential of the first film. If the dye material is properly selected such that the half-cell potential change will overlap at least a portion of the potential range wherein the dye material undergoes a transition in optical properties, a radiant energy transmission affect, i.e., a filtering effect, will be achieved. Examples of suitable reversible electrochemical reduction-oxidation systems are set forth in Table 1.

100% reduced and 100% oxidized states, and the application of external potential to achieve that particular electrical potential, by oxidation or reduction of a certain percentage of the first ionic species, a change in color, and therefore a change in optical transmission, will result.

The dye which is added to the first film will come to an equilibrium in which its potential is the same as that of the potential in the first film. As indicated above, if a dye is chosen having the proper half-cell potential

TABLE 1

TYPICAL REVERSIBLE ELECTROCHEMICAL REACTIONS

| Acid Media | Half Cell Potential |
|---|---|
| 1. $Cr^{+2} \rightarrow Cr^{+3} + e$ | 0.410 volts |
| 2. $Ti^{+2} \rightarrow Ti^{+3} + e$ | 0.370 volts |
| 3. $V^{+2} \rightarrow V^{+3} + e$ | 0.255 volts |
| 4. $Ti^{+3} + H_2O \rightarrow TiO^2 + 2H^+ + e$ | 0.100 volts |
| 5. $Sn^{+2} \rightarrow Sn^{+4} + 2e$ | −0.150 volts |
| 6. $Cu^+ \rightarrow Cu^{+2} + e$ | −0.153 volts |
| 7. $U^{+4} + 2H_2O \rightarrow UO_2^{+2} + 4H^+ + 2e$ | −0.062 volts |
| 8. $V^{+3} + H_2O \rightarrow VO^{+2} + 2H^+ + e$ | −0.361 volts |
| 9. $MnO_4^{-2} \rightarrow MnO_4^{-1} + e$ | −0.564 volts |
| 10. $Fe^{+2} \rightarrow Fe^{+3} + e$ | −0.771 volts |
| 11. $Hg_2^{+2} \rightarrow 2Hg^{+2} + 2e$ | −0.920 volts |
| 12. $ClO_3^- + H_2O \rightarrow ClO_4^- + 2H^+ + 2e$ | −1.190 volts |
| Basic Solution | |
| 1. $HPO_3^{-2} + 3OH^- \rightarrow PO_4^{-3} + 2H_2O + 2e$ | 1.120 volts |
| 2. $S_2O_4^{-2} + 4OH^- \rightarrow 2SO_3^{-2} + 2H_2O + 2e$ | 1.120 volts |
| 3. $CN^- + 2OH^- \rightarrow CNO^- + H_2O + 2e$ | 0.970 volts |
| 4. $SO_3^{-2} + 2OH^- \rightarrow SO_4^{-2} + H_2O + 2e$ | 0.930 volts |
| 5. $HSnO_2^- + H_2O + 3OH^- \rightarrow Sn(OH)_6^{-2} + 2e$ | 0.900 volts |
| 6. $SeO_3^{-2} + 2OH^- \rightarrow SeO_4 + H_2O + 2e$ | −0.050 volts |
| 7. $I^- + 6OH^- \rightarrow IO_3^- + 3H_2O + 6e$ | −0.260 volts |
| 8. $ClO_2^- + 2OH^- \rightarrow ClO_3^- + H_2O + 2e$ | −0.330 volts |
| 9. $ClO_3^- + 2OH^- \rightarrow ClO_4^- + H_2O + 2e$ | −0.360 volts |
| 10. $Br^- + 6OH^- \rightarrow BrO_3^- + 3H_2O + 6e$ | −0.610 volts |
| 11. $ClO^- + 2OH^- \rightarrow ClO_2^- + H_2O + 2e$ | −0.660 volts |
| 12. $IO_3^- + 3OH^- \rightarrow H_3IO_6^{-2} + 2e$ | −0.700 volts |
| 13. $Br^- + 2OH^- \rightarrow BrO^- + H_2O + 2e$ | −0.760 volts |
| 14. $3OH^- \rightarrow HO_2^- + H_2O + 2e$ | −0.880 volts |
| 15. $Cl^- + 2OH^- \rightarrow ClO^- + H_2O + 2e$ | −0.890 volts |

Referring to FIG. 3, the variation of half-cell potential as a function of percent oxidation for various reduction-oxidation systems can be seen. The various curves illustrate not only the half-cell potential for the 100% reduced or 100% oxidized forms of the ionic species but also the potential for any mixture thereof. With reference to the ferrous ion-ferric ion system, the oxidation from a 100% ferrous ion state to a 100% ferric ion state represents an increase in potential of approximately 0.4 volts (i.e., from approximately 0.6 volts to approximately 1.0 volts). By incorporation of a dye material which starts to change color at a potential somewhere between the half-cell potentials of the range for color change, for the particular reduction-oxidation system chosen, a change, of sufficient magnitude, in the relative ratio of the oxidized and reduced species in the first film will cause a system color change. Examples of suitable dyes starting to change color at a particular electrical potential are shown in Table 2 wherein the half-cell potential ($E_0$) for color change is given with reference to the standard hydrogen electrode potential for the dye in a solution one normal in hydrogen ions. The electrical potential ($E_0$)-given ) given Table 2 is for when the dye is in an equilibrium condition, i.e., when the dye is substantially half-oxidized and half-reduced.

TABLE 2

| Indicator | $E_0$ at pH=0 | Color Change Oxidized | Color Change Reduced |
|---|---|---|---|
| Safranine T | 0.24 | red | colorless |
| Neutral red | 0.24 | red | colorless |
| Indigo monosulforate | 0.26 | blue | colorless |
| Phenosafranine | 0.28 | red | colorless |
| Indigo tetrasulfenate | 0.36 | blue | colorless |
| Nile blue | 0.41 | blue | colorless |
| Methylene blue | 0.53 | green-blue | colorless |
| 1-Naphthol-2-sulfonic acid indophenol | 0.54 | red | colorless |
| 2,6-Dibromophenyl indophenol | 0.67 | blue | colorless |
| Diphenylamine (diphenylbenzidine) | 0.76 | violet | colorless |
| Diphenylamine sulfonic acid | 0.85 | red-violet | colorless |
| Erioglaucin A | 1.00 | red | green |
| Setoglaucin O | 1.06 | pale red | yellow-green |
| p-Nitrodiphenylamine | 1.06 | violet | colorless |
| o,m'-Diphenylamino dicarboxylic acid | 1.12 | blue-violet | colorless |
| o,o'-Diphenylamino dicarboxylic acid | 1.26 | blue-violet | colorless |

TABLE 2-continued

| Indicator | $E_0$ at pH=0 | Color Change Oxidized | Reduced |
|---|---|---|---|
| o-Phenanthroline ferrous complex | 1.14 | pale blue | red |
| Nitro-o-phenanthroline ferrous complex | 1.25 | pale blue | violet-red |

In view of the present invention and the disclosure of this specification, it is apparent that the dye diphenylamine (diphenylbenzidine) which, under the stated conditions, commences a color change from violet to a colorless state at a potential of approximately 0.76 volts would be suitable for use with the ferrous ion-ferric ion reduction-oxidation system.

Inasmuch as the change in the ratio of ionic species in the first film has associated therewith a corresponding change in pH, the dye material may be selected from that class of materials which are known to change color at a particular pH value, or, more particularly, over a suitable pH range. Hence, as used in the present invention, the term "half-cell potential" includes the special case wherein the half-cell potential is determined by the hydrogen ion activity as well as the more general case where the half-cell potential is determined by the ratio of the ion concentrations, such as the ferrous-ferric ion concentration ratio. Examples of suitable dyes changing color at known pH ranges, the pH range over which color change is effected, and the initial and final color states are given in Table 3.

With reference to Table 3, it should be noted that the reactions utilizing a basic solution do not directly involve the hydrogen ion. However, since in aqueous solutions, the hydroxyl ion and the hydrogen ion concentrations are directly related, the pH needed for color change can be produced by a corresponding change in the hydroxyl ion concentration.

TABLE 3

| pH Range | Indicator | Color Change Initial | Final |
|---|---|---|---|
| 0.0–2.0 | Malachite Green Hydrochloride | yellow | bluish green |
| 0.0–3.0 | Eosin Y | yellow | green |
| 0.0–3.6 | Erythrosin B | orange | red |
| 0.1–3.2 | Methyl Violet 2B | yellow | violet |
| 0.8–2.6 | Crystal Violet | green | blue violet |
| 1.2–2.1 | Diphenylaminobenzene | red | yellow |
| 1.2–2.8 | m-Cresol Purple | red | yellow |
| 1.2–2.8 | Thymol Blue | red | yellow |
| 1.2–2.8 | Xylenol Blue | red | yellow |
| 1.2–3.0 | Basic Fuchsin | purple | red |
| 1.3–4.0 | Benzopurpurin 4B | blue violet | red |
| 1.4–3.2 | Quinaldine Red | colorless | red |
| 2.0–3.0 | Cresol Red | orange | yellow |
| 2.4–4.0 | Methyl Yellow | red | yellow |
| 3.0–4.6 | Bromophenol Blue | yellow | purple |
| 3.0–4.6 | Chlorophenol Blue | yellow | blue |
| 3.0–4.6 | Tetrabromophenol Blue | yellow | blue |
| 3.0–6.0 | Phenacciolin | yellow | red |
| 3.2–4.8 | Bromochlorophenol Blue | yellow | purple |
| 3.4–4.9 | Propyl Orange | red orange | yellow |
| 3.7–5.0 | Benzene-azo-a-naphthylamine | red | yellow |
| 3.8–5.4 | Bromocresol Green | yellow | blue |
| 3.8–6.6 | Gallcin | light brown | rose |
| 4.0–7.0 | Chrysoidin Y | orange | yellow |
| 4.4–6.2 | Methyl Red | red | yellow |
| 4.5–8.3 | Azolitmin | red | blue |
| 4.7–6.2 | Cochineal | red | violet |
| 4.8–6.4 | Chlorophenol Red | yellow | red |
| 5.0–6.0 | Hematoxylin | yellow | red |
| 5.2–6.8 | Bromocresol Purple | yellow | purple |
| 5.2–7.0 | Bromophenol Red | yellow | red |
| 5.7–6.8 | Hematein | yellow | pink |
| 6.0–7.6 | Bromothymol Blue | yellow | blue |
| 6.0–8.4 | Naphthylamine Brown | orange | pink |
| 6.8–8.0 | Neutral Red | red | yellow orange |
| 6.8–8.4 | Phenol Red | red | yellow |
| 6.9–8.0 | Rosolic Acid | yellow | red |
| 7.2–8.8 | Cresol Red | yellow | red |
| 7.4–8.6 | Tumeric | yellow | brown |
| 7.4.–9.0 | m-Cresol Purple | red | yellow |
| 8.0–9.6 | Thymol Blue | yellow | blue |
| 8.0–9.6 | Xylenol Blue | yellow | blue |
| 8.3–10.0 | Phenolphthalein | colorless | red |
| 9.0–13.0 | Nile Blue A | blue | pink |
| 9.4–14.0 | Alkali Blue 6B | light blue | rose |
| 10.0–11.0 | Aniline Blue | blue | lavender |
| 10.0–13.0 | Phenacetolin | red | colorless |
| 10.1–12.1 | Alizarin Yellow G | yellow | orange |
| 11.1–12.7 | Tropacolin O | yellow orange | |
| 11.5–14.0 | Orange G | yellow | pink |
| 11.6–14.0 | Basic Fuchsin | red | colorless |
| 12.0–13.0 | Aniline Blue | pink | orange red |
| 12.0–14.0 | Acid Fuchsin | red | colorless |
| 12.1–14.0 | Clayton Yellow | yellow | red |

The basic principle of the present invention may be best described with reference to a particular embodiment thereof. In the first film 12 of filter 10, a small amount (for example, $1 \times 15^{-5}$ to $1 \times 10^{-2}$ moles) of a dye, such as diphenylbenzidene, is dispersed in its reduced colorless state along with a suitable concentration (for example, about $1 \times 10^{-3}$ molar to 1 molar) of ferrous sulfate. In second film 13, a similar, prefereably equal, concentration of a ferric salt, such as ferric sulfate, is disolved. If a potential slightly in excess of the open circuit cell potential is applied through the filter from an external source, as by closing switch 23, the ferrous ions are oxidized to ferric ions in first film 12, while the ferric ions in second film 13 are reduced to ferrous ions. Initially, the half-cell potential in first film 12 is about 0.55 volts (see FIG. 3) which is well below the half-cell potential of the diphenylbenzidene (about 0.76 volts) at about which a color change commences to take place. Since the dye assumes the same electrical potential as the solution in which it is disolved, the dye remains in its reduced colorless state when added to the ferrous system and will remain colorless until such time as its color changing potential is reached. With the application of an external potential, the ferrous ions are oxidized and the half-cell potential of first film 12 increases. Thus, when the concentration of the ferric and ferrous ions approach each other (i.e., when the system approaches the standard half-cell potential of about 0.771 volts), the dye starts to change to color since its particular color changing potential has been exceeded. If desired, the current can be permitted to continue to pass through the filter 10 until the ferrous ions in the first film 12 are completely oxidized to ferric ions and, conversely, the ferric ions in the second film 13 are completely converted to ferrous ions. At that time, no further current will flow since there are no further ions to be oxidized or reduced, and the electrical potential of the first film will be about 1.0 volts (see FIG. 3). If the external potential is terminated, the static potential difference will be maintained since the barrier means prevents passage of the first ionic species and the second ionic species which are those species related by the reversible electrochemical reaction. The color developed in the system will be maintained until such time as an external potential is applied in such a manner as to cause further color change in accordance with the the technique described herein.

If desired, this electrochemical process whereby color change is effected can be stopped at any point at which the desired amount of transmission of radiant energy is achieved. In other words, the degree of color change and, consequently, the amount of radiant energy transmission can be regulated. If the direction of current flow is then reversed, the reverse reactions occur and the system can be operated to return to an intermediate state or to its initial state. In the present example, the half-cell potential of first film 12 can be reduced below the particular half-cell potential at which the diphenylbenzidene changes color whereby the system will be reconverted to its initial colorless state.

In addition to the above example, similar systems, including the dyes thionin or erioglaucine with copper, nickel, chromium or tin ions, have been used with comparable results. It should be understood, however, that the particular material chosen can be varied to suit the particular characteristics desired and that the foregoing materials are merely exemplary of the materials suitable for use with the present invention.

While the invention has been described with reference to preferred embodiments thereof, it will be understood by those skilled in the art that various changes may be made without departing from the true spirit and scope of the invention. Accordingly, all modifications to which the present invention is readily susceptible, without departing from the spirit and scope of this disclosure, are considered part of the present invention.

What is claimed is:

1. A radiant energy filter adapted to reversibly regulate the transmission of radiant energy therethrough comprising:
   an electrolytically conductive layer comprising,
      I. a first film having dispersed therein (a) a dye whose color commences to change at a particular half-cell potential and (b) a first ionic species which can have its oxidation state changed by the passage of current through said first film, said oxidation change causing a half-cell potential change in said first film which overlaps at least a portion of the half-cell potential at which said dye changes color;
      II. an adjacent second film having a second ionic species therein which has its oxidation state changed by the passage of current through said second film, said first ionic species and said second ionic species being related by a reversible reduction oxidation electrochemical reaction; and
      III. barrier means positioned between said first film and said second film, said barrier means adapted to prevent the passage therethrough of said dye, said first ionic species and said second ionic species but adapted to permit the passage therethrough of current-carrying ions, said current-carrying ions comprising a third ionic species common to both said first and second film, and
   first and second electrodes in contact with opposite sides of said electrolytically conductive layer.

2. The radiant energy filter of claim 1 wherein said first and second films are aqueous solutions.

3. The radiant energy filter of claim 1 wherein said first and second films are gel sheets and said barrier means comprises the interface between said sheets.

4. The radiant energy filter of claim 1 further including a first electrical connection to said first electrode and a second electrical connection to said second electrode, said first electrical connection being positioned at a first corner of said filter and said second electrical connection being positioned at a diagonally opposite corner of said filter whereby substantially uniform current density is achieved across said electrolytically conductive layer.

5. The radiant energy filter of claim 1 further including means for causing a current to pass through said filter, said current causing a particular ph to be established in said first film by a change in the ratio of said first ionic species to said ionic species therein as a result of the reduction-oxidation electrochemical reaction conducted therein during the passage of current through said filter whereby said dye changes color.

6. An electrolytic process for regulating the transmission of radiant energy comprising the steps of:
   a. passing the radiant energy to be regulated through a radiant energy filter, said filter comprising:

I. a first film having dispersed therein (a) a dye whose color commences to change at a particular half-cell potential and (b) a first ionic species which can have its oxidation state changed by the passage of current through said first film, said oxidation change causing a half-cell potential change in said first film which overlaps at least a portion of the half-cell potential at which said dye changes color;

II. an adjacent second film having a second ionic species therein which has its oxidation state changed by the passage of current through said second film, said first ionic species and said second ionic species being related by a reversible reduction-oxidation electrochemical reaction; and III. barrier means positioned between said first film and said second film, said barrier means adapted to prevent the passage therethrough of said dye, said first ionic species and said second ionic species but adapted to permit the passage therethrough of current-carrying ions, said current-carrying ions comprising a third ionic species common to both said first and second film; and IV. a first electrode in contact with said first film on one side of said filter and a second electrode in contact with said second film on the opposite side of said filter; and b. passing current through said filter to cause the color of said dye to change, the transmission of said radiant energy through said filter being regulated by the color of said dye.

7. The process of claim 6 further including the step of applying substantially uniform current density between said electrodes by making a first electrical connection to said first electrode and a second electrical connection to said second electrode, said first electrical connection being positioned at one corner of said first electrode and said second electrical connection being positioned at the diagonally opposite corner of said second electrode.

8. The process of claim 6 further including the step of terminating the passage of current through said filter when a desired color state is reached, said desired color state being maintained in the absence of further current applied to said filter.

9. The process of claim 8 further including the step of passing current through said filter in an opposite direction after said desired current state is reached whereby the color of said dye will be returned to its initial color state or to a color state between said desired color state and said initial color state.

* * * * *